US011576483B2

(12) United States Patent
Jimenez et al.

(10) Patent No.: US 11,576,483 B2
(45) Date of Patent: Feb. 14, 2023

(54) ORAL CARE IMPLEMENT HAVING MULTIPLE SOFT TISSUE CLEANER COMPONENTS

(71) Applicant: Colgate-Palmolive Company, New York, NY (US)

(72) Inventors: Eduardo Jimenez, Manalapan, NJ (US); Michael Rooney, Millburn, NJ (US); Robert Moskovich, Manakin-Sabot, VA (US); Jacob Pringiers, Colombo (LK); Luca Casini, Milan (IT); Joachim Storz, Zell am See (AT); Raimund Klausegger, Vienna (AT)

(73) Assignee: Colgate-Palmolive Company, New York, NY (US)

( * ) Notice: Subject to any disclaimer, the term of this patent is extended or adjusted under 35 U.S.C. 154(b) by 1057 days.

(21) Appl. No.: 16/257,897

(22) Filed: Jan. 25, 2019

(65) Prior Publication Data

US 2019/0150603 A1  May 23, 2019

Related U.S. Application Data

(60) Continuation of application No. 15/401,607, filed on Jan. 9, 2017, now Pat. No. 10,231,536, which is a
(Continued)

(51) Int. Cl.
*A46B 15/00* (2006.01)
*B29C 45/22* (2006.01)
(Continued)

(52) U.S. Cl.
CPC ...... *A46B 15/0081* (2013.01); *A46B 15/0055* (2013.01); *A61B 17/244* (2013.01);
(Continued)

(58) Field of Classification Search
CPC ............ A46B 15/0081; A46B 15/0055; A46B 2200/1066; A46B 3/00; A46B 5/0025;
(Continued)

(56) References Cited

U.S. PATENT DOCUMENTS 3,337,893 A   8/1967   Fine et al.
4,517,701 A   5/1985   Stanford, Jr.
(Continued)

FOREIGN PATENT DOCUMENTS

DE   202005009026   10/2005
DE   102008025825   12/2007
(Continued)

OTHER PUBLICATIONS

International Search Report in International Application No. PCT/US2009/068614, dated Apr. 29, 2011. WO.

*Primary Examiner* — David J Walczak

(57) ABSTRACT

An oral care implement with a soft tissue cleaner. The oral care implement may include a handle and a head, the head having a first surface, and an opposite second surface, and a peripheral surface extending between the first and second surfaces. A soft tissue cleaner may have a first cleaner fixed to the second surface of the head and a second cleaner fixed to the peripheral surface of the head. Furthermore, a second cleaner may incorporate a plurality of grooves extending at least a portion of the distance from the first surface to the second surface along the peripheral surface.

12 Claims, 9 Drawing Sheets

Related U.S. Application Data continuation of application No. 13/948,546, filed on Jul. 23, 2013, now Pat. No. 9,586,350, which is a division of application No. 12/641,686, filed on Dec. 18, 2009, now Pat. No. 8,500,766.

(51) Int. Cl.

| | | |
|---|---|---|
| *A61B 17/24* | (2006.01) | |
| *B29C 45/16* | (2006.01) | |
| *B29C 45/14* | (2006.01) | |
| *B29L 31/42* | (2006.01) | |
| *B29K 23/00* | (2006.01) | |
| *B29K 25/00* | (2006.01) | |

(52) U.S. Cl.
CPC .... *B29C 45/1418* (2013.01); *B29C 45/14336* (2013.01); *B29C 45/1676* (2013.01); *B29C 45/22* (2013.01); *A46B 2200/1066* (2013.01); *B29C 2045/14352* (2013.01); *B29K 2023/12* (2013.01); *B29K 2025/08* (2013.01); *B29L 2031/425* (2013.01)

(58) Field of Classification Search
CPC ..... A46B 9/02; B29C 45/22; B29C 45/14336; B29C 45/1676; B29C 45/1418; B29C 2045/14352; A61B 17/244; B29L 2031/425; B29K 2023/12; B29K 2025/08
USPC ............ 401/268, 270; 15/159.1, 190, 191.1, 15/207.2
See application file for complete search history.

(56) References Cited

U.S. PATENT DOCUMENTS

| | | | |
|---|---|---|---|
| 4,959,052 | A | 9/1990 | Cox |
| 5,226,197 | A | 7/1993 | Nack et al. |
| 5,331,704 | A | 7/1994 | Rosen et al. |
| 5,497,526 | A | 3/1996 | Klinkhammer |
| 5,604,951 | A | 2/1997 | Shipp |
| D390,706 | S | 2/1998 | Hohlbein et al. |
| 5,758,383 | A | 6/1998 | Hohlbein |
| D404,205 | S | 1/1999 | Hohlbein |
| D404,206 | S | 1/1999 | Hohlbein |
| 5,863,102 | A | 1/1999 | Waguespack et al. |
| 5,946,758 | A | 9/1999 | Hohlbein et al. |
| 5,991,958 | A | 11/1999 | Hohlbein |
| 6,041,468 | A | 3/2000 | Chen et al. |
| 6,073,299 | A | 6/2000 | Hohlbein |
| 6,088,870 | A | 7/2000 | Hohlbein |
| D429,887 | S | 8/2000 | Hohlbein et al. |
| 6,119,296 | A | 9/2000 | Noe et al. |
| 6,131,228 | A | 10/2000 | Chen et al. |
| 6,276,021 | B1 | 8/2001 | Hohlbein |
| D450,457 | S | 11/2001 | Hohlbein |
| 6,314,606 | B1 | 11/2001 | Hohlbein |
| D451,286 | S | 12/2001 | Hohlbein |
| 6,352,545 | B1 | 3/2002 | Wagner |
| D456,138 | S | 4/2002 | Hohlbein |
| D456,139 | S | 4/2002 | Hohlbein |
| D457,323 | S | 5/2002 | Hohlbein |
| 6,402,494 | B1 | 6/2002 | Lanvers |
| D461,313 | S | 8/2002 | Hohlbein |
| 6,442,787 | B2 | 9/2002 | Hohlbein |
| D464,133 | S | 10/2002 | Barnett et al. |
| D474,608 | S | 5/2003 | Hohlbein |
| 6,599,048 | B2 | 7/2003 | Kuo |
| 6,658,688 | B2 | 12/2003 | Gavney, Jr. |
| D486,649 | S | 2/2004 | Sprosta et al. |
| 6,820,299 | B2 | 11/2004 | Gavney, Jr. |
| 6,820,300 | B2 | 11/2004 | Gavney, Jr. |
| 6,859,969 | B2 | 3/2005 | Gavney, Jr. et al. |
| D503,538 | S | 4/2005 | Desalvo |
| 6,886,207 | B1 | 5/2005 | Solanki |
| 6,895,629 | B1 | 5/2005 | Wenzler |
| D511,249 | S | 11/2005 | Hohlbein |
| D513,882 | S | 1/2006 | Hohlbein et al. |
| D514,320 | S | 2/2006 | Hohlbein |
| D514,812 | S | 2/2006 | Hohlbein et al. |
| 6,996,870 | B2 | 2/2006 | Hohlbein |
| D516,819 | S | 3/2006 | Hohlbein |
| D517,812 | S | 3/2006 | Hohlbein et al. |
| D517,813 | S | 3/2006 | Hohlbein et al. |
| 7,007,332 | B2 | 3/2006 | Hohlbein |
| 7,020,928 | B2 | 4/2006 | Hohlbein |
| D520,753 | S | 5/2006 | Hohlbein |
| 7,047,591 | B2 | 5/2006 | Hohlbein |
| 7,069,615 | B2 | 7/2006 | Gavney, Jr. |
| 7,089,621 | B2 | 8/2006 | Hohlbein |
| D527,528 | S | 9/2006 | Hohlbein |
| D528,803 | S | 9/2006 | Hohlbein |
| D532,202 | S | 11/2006 | Hohlbein |
| D532,607 | S | 11/2006 | Hohlbein |
| 7,143,462 | B2 | 12/2006 | Hohlbein |
| D535,823 | S | 1/2007 | Crossman |
| 7,168,125 | B2 | 1/2007 | Hohlbein |
| 7,181,799 | B2 | 2/2007 | Gavney, Jr. et al. |
| 7,182,542 | B2 | 2/2007 | Hohlbein |
| 7,213,288 | B2 | 5/2007 | Hohlbein |
| 7,219,384 | B2 | 5/2007 | Hohlbein |
| 7,273,327 | B2 | 9/2007 | Hohlbein et al. |
| D557,504 | S | 12/2007 | Hohlbein |
| D557,505 | S | 12/2007 | Hohlbein |
| 7,310,846 | B1 | 12/2007 | Archibeque |
| 7,322,067 | B2 | 1/2008 | Hohlbein |
| D562,560 | S | 2/2008 | Hohlbein |
| 7,331,731 | B2 | 2/2008 | Hohlbein et al. |
| D566,401 | S | 4/2008 | Crossman |
| 7,386,909 | B2 | 6/2008 | Hohlbein |
| 7,458,125 | B2 | 12/2008 | Hohlbein |
| 7,472,448 | B2 | 1/2009 | Hohlbein et al. |
| 7,478,959 | B2 | 1/2009 | Hohlbein |
| 7,480,955 | B2 | 1/2009 | Hohlbein et al. |
| D589,260 | S | 3/2009 | Hohlbein |
| D598,199 | S | 8/2009 | Russell et al. |
| D599,556 | S | 9/2009 | Russell et al. |
| 7,594,293 | B2 | 9/2009 | Xi et al. |
| 7,614,111 | B2 | 11/2009 | Moskovich |
| 7,721,376 | B2 | 5/2010 | Hohlbein et al. |
| 7,722,274 | B2 | 5/2010 | Hohlbein et al. |
| 7,725,980 | B2 | 6/2010 | Moskovich |
| 7,735,174 | B2 | 6/2010 | Hohlbein et al. |
| 7,841,041 | B2 | 11/2010 | Moskovich |
| 7,845,042 | B2 | 12/2010 | Moskovich |
| 7,908,699 | B2 | 3/2011 | Hohlbein et al. |
| 8,109,686 | B2 * | 2/2012 | Bartschi ............ A46B 11/0062 401/270 |
| 8,151,397 | B2 | 4/2012 | Moskovich |
| 8,382,208 | B2 | 2/2013 | Baertschi |
| 8,448,287 | B2 * | 5/2013 | Ponzini ................ A61C 17/222 15/176.1 |
| 9,398,804 | B2 | 7/2016 | Cai et al. |
| 2003/0077107 | A1 * | 4/2003 | Kuo ........................ A46B 17/08 401/187 |
| 2003/0191417 | A1 | 10/2003 | Welt et al. |
| 2004/0128780 | A1 | 7/2004 | Chan |
| 2004/0255416 | A1 | 12/2004 | Hohlbein |
| 2005/0015907 | A1 | 1/2005 | Georgi |
| 2005/0053898 | A1 | 3/2005 | Ghosh et al. |
| 2005/0210612 | A1 | 9/2005 | Hohlbein |
| 2005/0249900 | A1 | 11/2005 | Barre |
| 2006/0085932 | A1 | 4/2006 | Santos |
| 2006/0129171 | A1 | 6/2006 | Moskovich |
| 2006/0195995 | A1 | 9/2006 | Moskovich et al. |
| 2006/0200925 | A1 | 9/2006 | Moskovich et al. |
| 2007/0151575 | A1 | 7/2007 | De Masi, Sr. |
| 2007/0163064 | A1 | 7/2007 | Wong |
| 2007/0174985 | A1 | 8/2007 | Steven, Jr. |
| 2008/0103597 | A1 | 5/2008 | Lechmann et al. |
| 2008/0147104 | A1 | 6/2008 | Gatzemeyer et al. |
| 2008/0201884 | A1 | 8/2008 | Vazquez et al. |

(56) References Cited

U.S. PATENT DOCUMENTS

2010/0043162 A1 2/2010 Zimmermann et al.
2010/0257683 A1 10/2010 Boyd .................... A46B 9/005
 15/167.1
2011/0152909 A1 6/2011 Jimenez

FOREIGN PATENT DOCUMENTS

| WO | WO 00/15077 | 3/2000 |
| WO | WO 07/051203 | 5/2007 |
| WO | WO 08/093300 | 8/2008 |
| WO | WO 08/103597 | 8/2008 |

* cited by examiner

ORAL CARE IMPLEMENT HAVING MULTIPLE SOFT TISSUE CLEANER COMPONENTS

CROSS-REFERENCE TO RELATED APPLICATIONS

This application is a continuation of U.S. application Ser. No. 15/401,607, filed Jan. 9, 2017, which is a continuation of U.S. application Ser. No. 13/948,546, filed Jul. 23, 2013, now U.S. Pat. No. 9,586,350, which is a divisional of U.S. application Ser. No. 12/641,686, filed Dec. 18, 2009, now U.S. Pat. No. 8,500,766, the entireties of which are incorporated herein by reference.

BACKGROUND OF THE INVENTION

According to the American Dental Association, a major source of bad breath in healthy people is microbial deposits on the tongue, where a bacterial coating harbors organisms and debris that contribute to bad breath. The tongue is a haven for the growth of microorganisms since the papillary nature of the tongue surface creates a unique ecological site that provides an extremely large surface area, favoring the accumulation of oral bacteria. Anaerobic flora and bacteria residing on the tongue play an important role in the development of chronic bad breath commonly called halitosis. In general, the bacteria produce volatile sulfur compounds (VSC). If there is enough buildup of the sulfur compounds, the result can be bad breath or oral malodor.

While bladed tongue scrapers have been used in the past, these scrapers are inadequate in respect to their effectiveness on the soft tissue surface of the tongue. Broad flat scraping blades are limited in their ability to reach between the papillae where the bacteria and micro debris have collected. Moreover, notwithstanding the benefits to be gained by any ability to clean the tongue, some users avoid the use of such blades because of lack of comfort on the tongue surface.

Recently, substantial efforts have been expended to develop oral care implements having improved soft tissue cleaners. An example of such an oral care implement has a tissue cleaner in the form of a pad composed of an elastomeric material. The pad is disposed on the head on a surface opposite the tooth cleaning elements. The pad includes a plurality of conically shaped nubs extending therefrom for cleaning between the papillae of the tongue. While this oral care implement provides a substantial improvement over the then existing tongue cleaners, it is somewhat limited in that the pad of elastomeric material is provided on only one major surface of the head. Therefore, the soft tissue pad cannot reach into tight spaces and recesses within the oral cavity.

A further improvement of oral care implements incorporating soft tissue cleansing technology has a head having a single elastomeric soft tissue cleaner applied to the major rear surface of the head that also extends along the side walls of the head. This arrangement allows the soft tissue cleaners to act on the user's gums during brushing.

A limiting factor in versatility of the soft tissue cleaner on the head of oral care implements, thus far, has been the inability to cost-effectively manufacture isolated multiple components on the head. This is in part due to the parametric requirements of existing injection molding equipment and processes.

Despite the aforementioned and other improvements, a need still exists for an oral care implement with a soft tissue cleaner that can provide effective removal of bacteria from the tongue and other oral soft tissue regions while maintaining comfort to the user.

SUMMARY OF THE INVENTION

The invention pertains to an oral care implement with a tissue cleaner that provides improved cleaning and effective removal of bacteria and micro debris disposed on oral tissue surfaces. The invention is an oral care implement comprising multiple soft tissue cleaners that offer expanded cleaning and/or in-mouth sensations during an oral care session. The oral care implement may include a handle and a head, the head having a first surface and an opposite rear surface. A first cleanser may be fixed to the first surface of the head such that the first cleanser has a hole through which a portion of the first surface of the head is exposed. Furthermore, a second cleanser may be fixed to the portion of the first surface of the head that is exposed through the hole of the first cleanser.

In one particular aspect, the invention may be an oral care implement comprising: a handle; a head connected to the handle, the head having a front surface and a rear surface opposite the front surface; a protuberance extending from the rear surface of the head; a first cleanser located on the rear surface of the head and having a hole extending therethrough, the protuberance extending into the hole of the first cleanser; and a second cleanser located on the protuberance.

In another aspect, the invention can be an oral care implement comprising: a handle; a head connected to the handle, the head having a first surface, a second surface, and a peripheral side surface extending between the first and second surfaces; a first cleanser fixed to the first surface of the head, the first cleanser being a pad having a hole extending therethrough; and a second cleanser fixed to a portion of the first surface of the head that is exposed through the hole of the first cleanser

BRIEF DESCRIPTION OF THE DRAWINGS

This invention is capable of use in a broad array of oral care implements and hygiene products. The drawings illustrate one use of the invention and are not to be construed as the only embodiment of the invention.

DETAILED DESCRIPTION OF THE DRAWINGS

In the following description, the invention is discussed in terms of a manual toothbrush. However, in other forms, the invention could be in the form of other oral care implements including a soft-tissue cleansing implement, a powered toothbrush, or other ansate implements designed for oral care.

Figure 1:
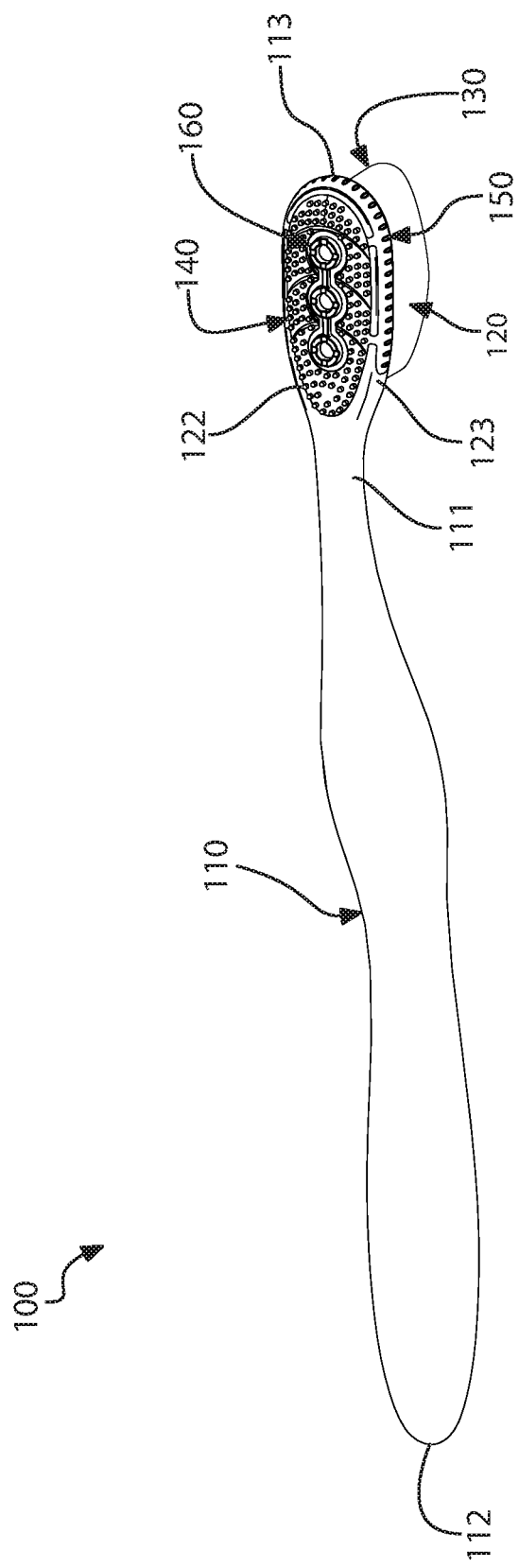
FIG. 1 is a rear perspective view of an ansate oral care implement according to one embodiment of the present invention.

Referring first to FIG. 1, a toothbrush 100 is illustrated according to one embodiment of the present invention. The toothbrush 100 generally comprises a handle 110 and a head 120. The handle 110 provides the user with a mechanism by which he/she can readily grip and manipulate the toothbrush 100. The handle 110 is generically illustrated and may be formed of many different shapes, sizes, materials and by a variety of manufacturing methods that are well-known to those skilled in the art. For example, the handle 110 can be constructed of elastomers, polypropylene, SAN, ABS, or even paper products such as a typical lollipop stick. If desired, the handle 110 may include a suitable textured grip (not shown) made of a thermoplastic elastomer or can be a multi-part construction. Stated simply, the details of the handle 110 are not limiting of the present invention and, thus, require no further discussion for purposes of the present invention.

The toothbrush 100 extends from a proximal end 112 to a distal end 113. The head 120 is operably connected to a distal end of the handle 110. Generally, the head 110 and the handle 120 of the toothbrush are preferably formed as a single unitary structure using a molding, milling, machining or other suitable process. However, in other embodiments, the handle 110 and head 120 may be formed as separate components which are operably connected at a later stage of the manufacturing process by any suitable technique known in the art, including without limitation thermal welding, a tight-fit assembly, a coupling sleeve, adhesion, or fasteners. Whether the head 120 and handle 110 are of a unitary or multi-piece construction (including connection techniques) is not limiting of the present invention.

It should be noted at this time that relative terms such as distal, middle, proximal, upper, lower, top, bottom, left, right etc. are merely used to delineate relative positions of the components of the toothbrush 100 with respect to one another and are not intended to be in any further way limiting of the present invention.

The head 120 generally comprises a front surface 121, a rear surface 122 and a peripheral surface 123. The peripheral surface 123 connects the front and rear surfaces 121, 122. The front surface 121, the rear surface 122 and the peripheral surface 123 of the head 120 can take on a wide variety of shapes and contours, none of which are limiting of the present invention. For example, the surfaces can be planar, contoured or combinations thereof. Furthermore, while the head 120 is normally widened relative to the neck 111 of the handle 110, it could in some constructions simply be a continuous extension or narrowing of the handle 110.

Figure 3:
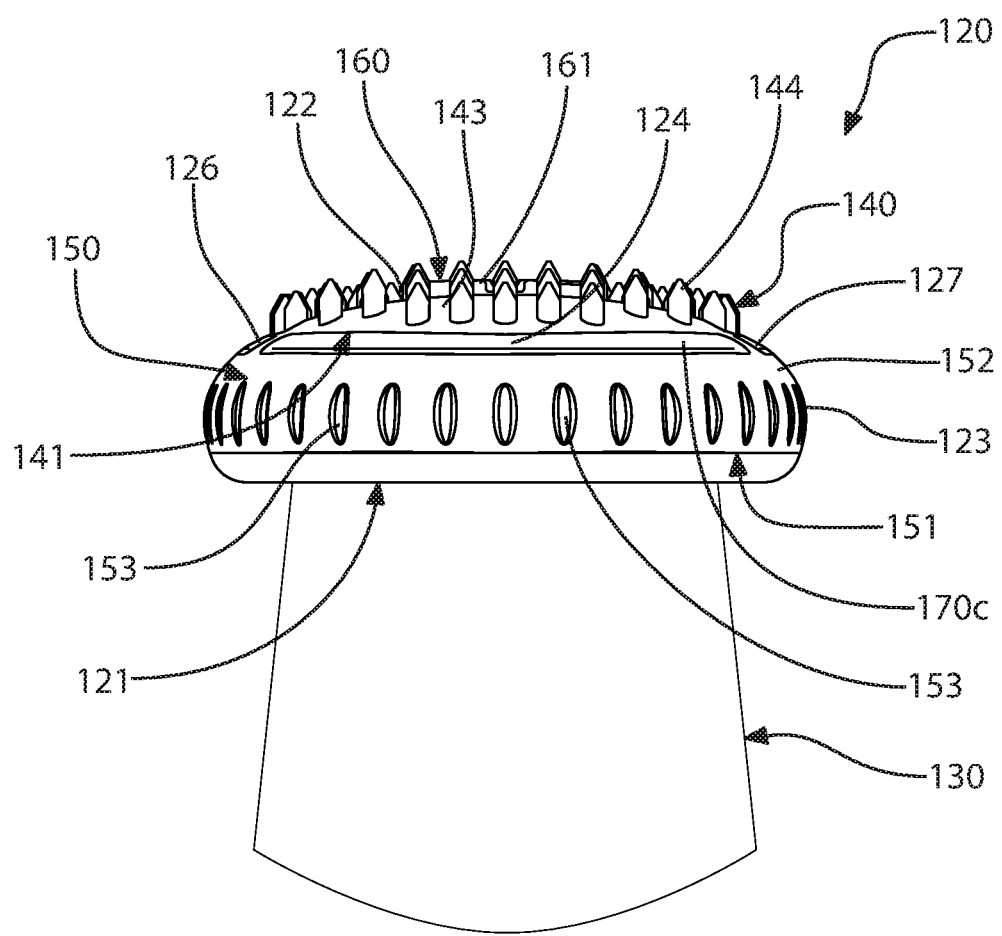
FIG. 3 is a top view of the head of the ansate oral care implement of FIG. 1.
Figure 4:
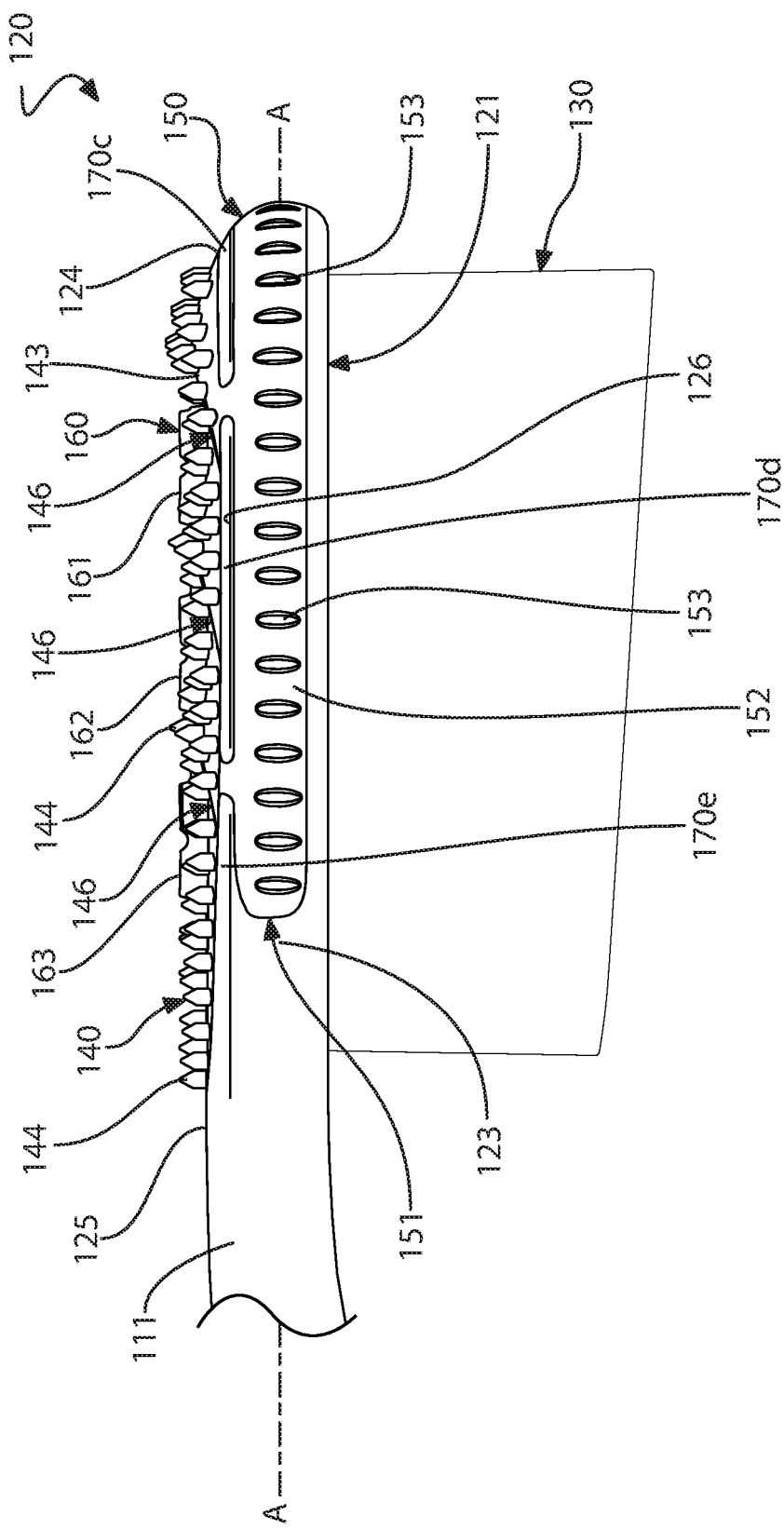
FIG. 4 is a left-side view of the head of the ansate oral care implement of FIG. 1.

The front surface 121 (best visible in FIG. 3) comprises a collection of cleaning elements 130 extending therefrom for cleaning contact with an oral surface. While the collection of cleaning elements 130 is particularly suited for brushing teeth, the collection of cleaning elements 130 can also be used to clean oral soft tissue, such as a tongue, gums, or cheeks instead of or in addition to teeth. As used herein, the term "cleaning element" is used in a generic sense to refer to any structure that can be used to clean or massage an oral surface through relative surface contact. Common examples of "cleaning elements" include, without limitation, filament bristles, fiber bristles, nylon bristles, spiral bristles, rubber bristles, elastomeric protrusions, flexible polymer protrusions, combinations thereof and/or structures containing such materials or combinations. The focus of the present invention is on the arrangement of the soft tissue cleaner (which in the illustrated embodiment includes three components 140, 150, 160) on head 120 of the toothbrush 100. Thus, the collection 130 of tooth cleaning elements on the front surface 121 of the head are illustrated generically with the understanding that any desired configuration can be incorporated into the toothbrush 100.

Figure 2:
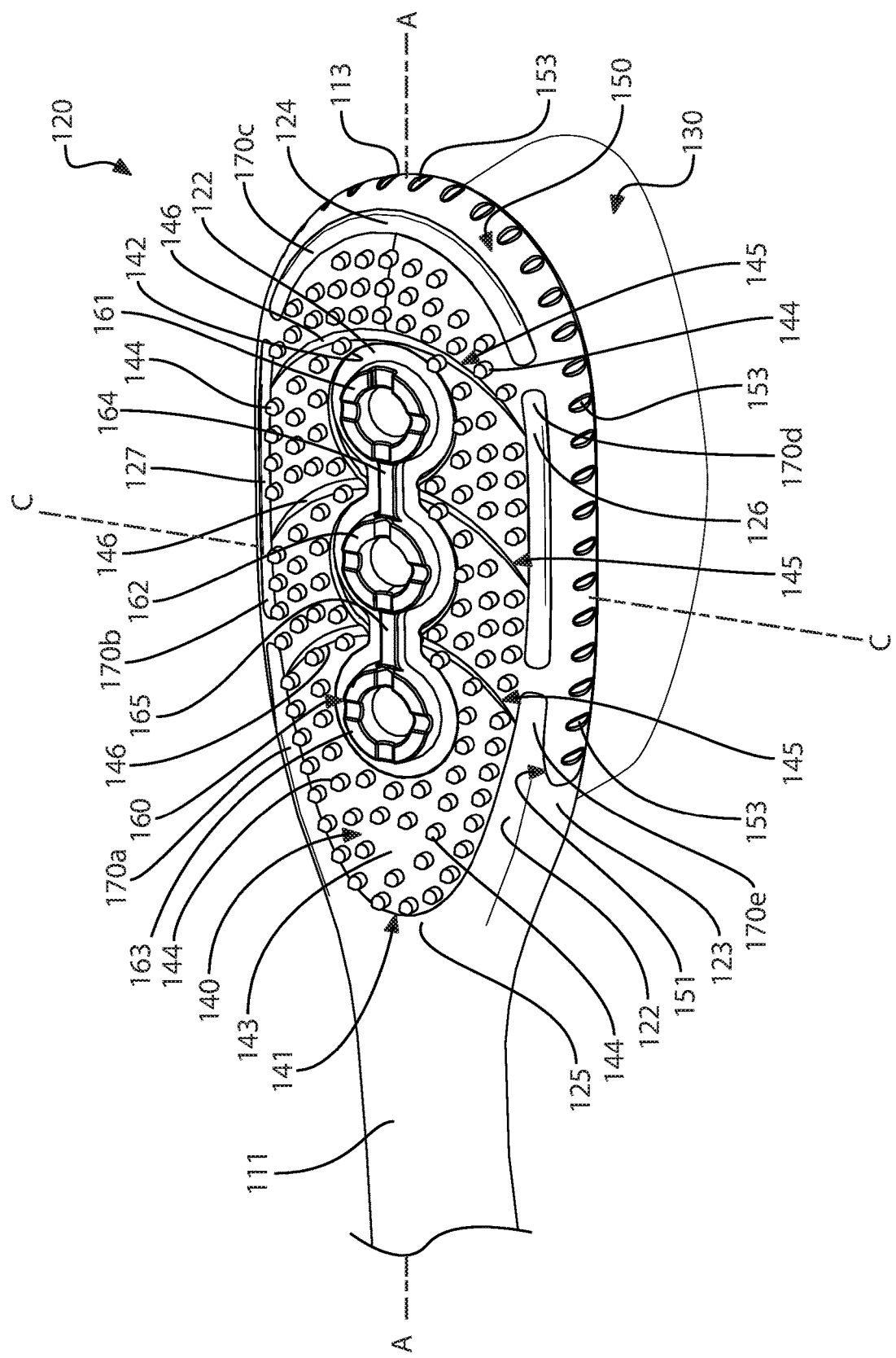
FIG. 2 is a close-up view of the head of the ansate oral care implement of FIG. 1.

Referring now to FIG. 2, a close-up view of the head 120 of the toothbrush 100 is illustrated. The head 120 generally comprises a first soft tissue cleaner 140, a second soft tissue cleaner 160 and a third soft tissue cleaner 150. The soft tissue cleaners 140, 150, 160 are preferably constructed of a biocompatible resilient material suitable for uses in an oral hygiene apparatus, such as a thermoplastic elastomer. As an example, one preferred elastomeric material is styrene-ethylene/butylene-styrene block copolymer (SEBS) manufactured by GLS Corporation. Nevertheless, SEBS material from other manufacturers or other materials. The soft tissue cleaners 140, 150, 160 can be constructed of different types of resilient materials or the same resilient material with one or more different characteristics, such as color, hardness, density, flavor, and/or sensate.

Figure 5:
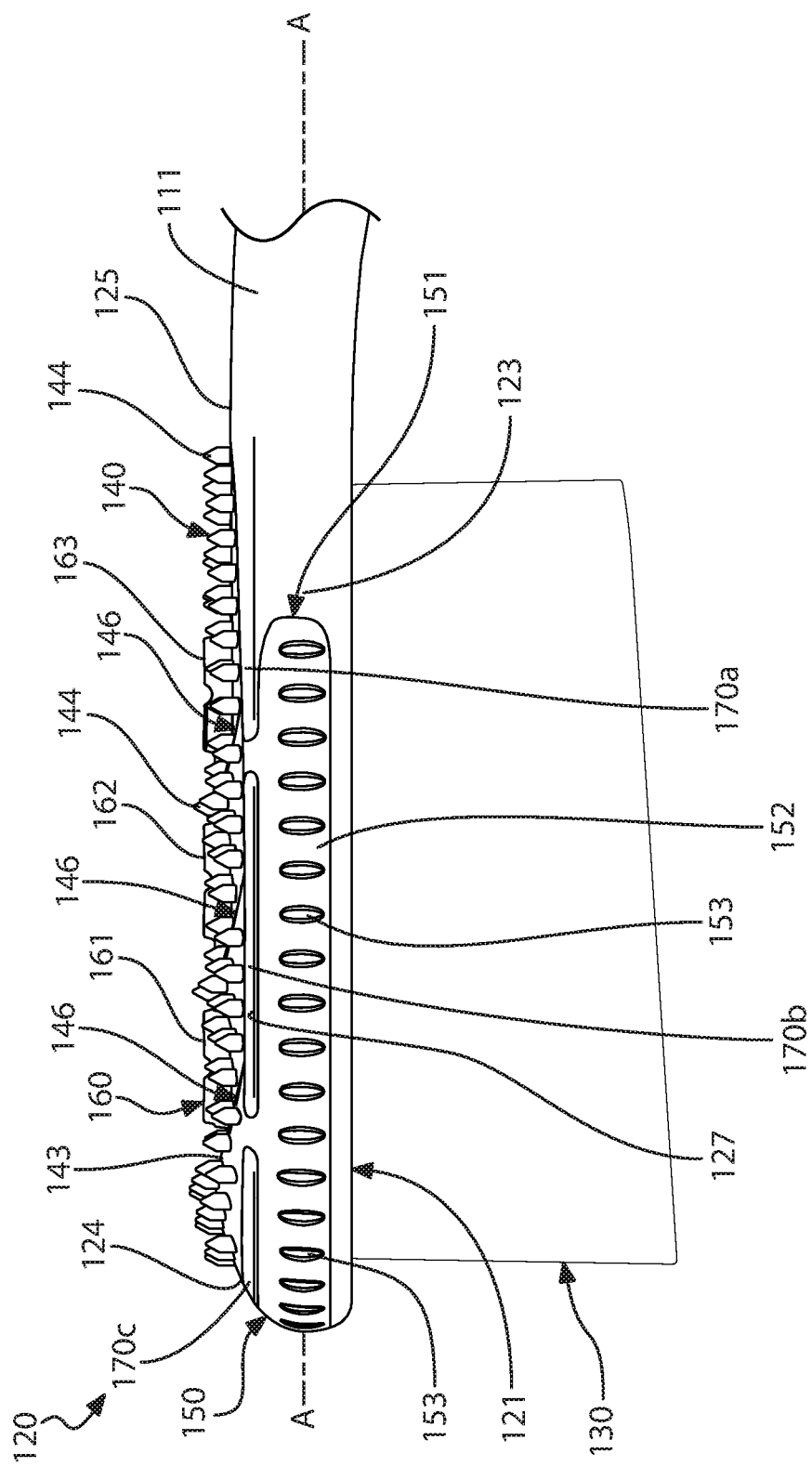
FIG. 5 is a right-side view of the head of the ansate oral care implement of FIG. 1.
Figure 6:
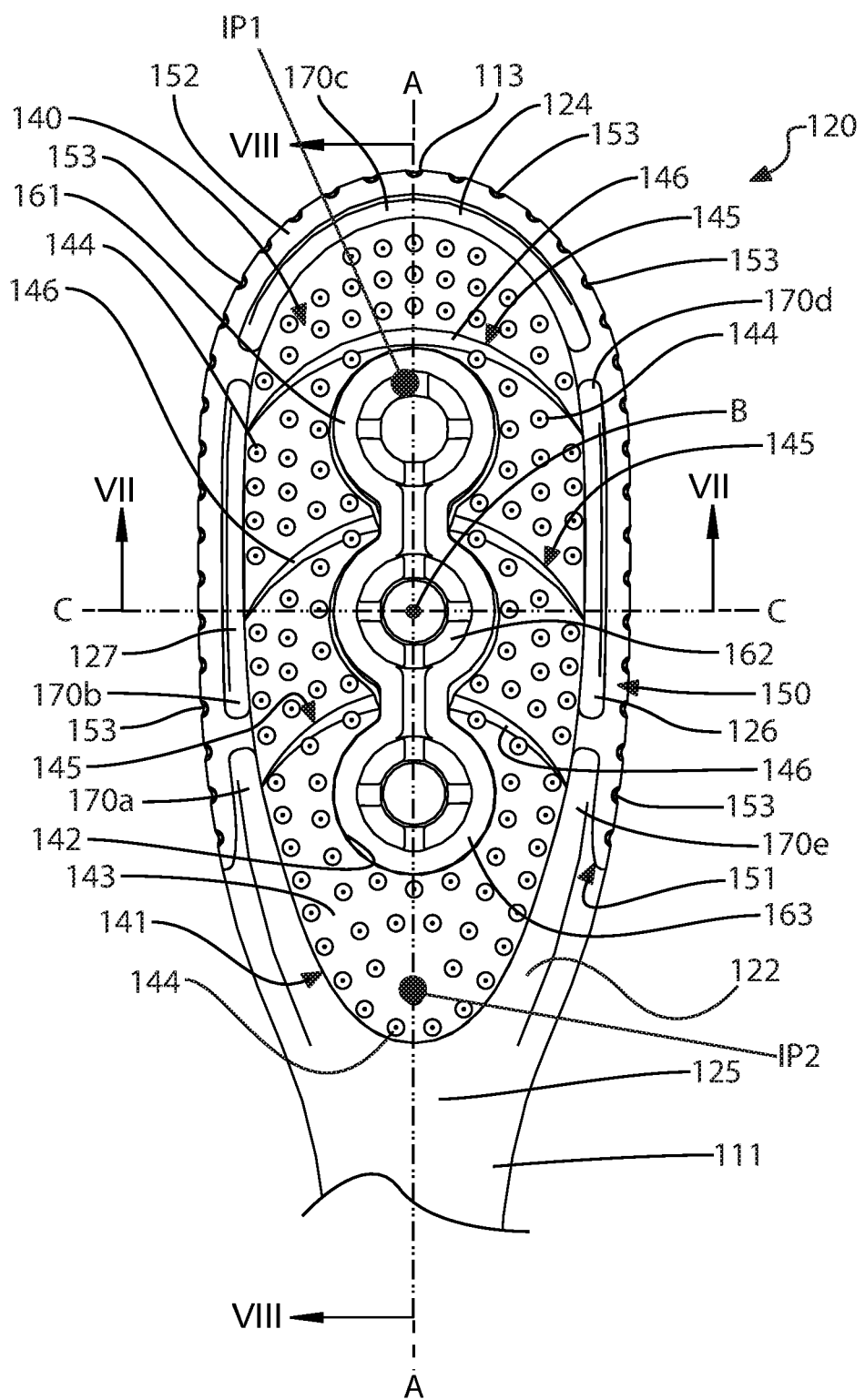
FIG. 6 is a rear view of the head of the ansate oral care implement of FIG. 1.

With reference to FIGS. 2, 5 and 6 concurrently, the details of the soft tissue cleaner 140 will now be discussed. The first soft tissue cleaner 140 is in the form of a pad 141 that is fixed to the rear surface 122 of the head 120 of the toothbrush 100. The pad 141 is preferably molded directly to the head 120 but can be molded separately and later fixed to the head 120 if desired, for example by an adhesive or sonic welding. The pad 141 extends from a distal end 124 of the head 120 to a proximal end 125 of the head 120 and covers substantially the entire width of the head 120, extending from the first lateral edge 126 of the head to the second lateral edge 127 of the head 120.

The pad 141 has a central hole 142 extending therethrough. As a result, the pad 141 takes on an annular shape. In the illustrated embodiment, the central hole 142 is an elongated shape comprising three overlapping and aligned circular portions. The central hole 142 is preferably shaped to generally correspond to the shape of the second soft tissue cleaner 160. The invention, however, is not so limited. Moreover, while a single hole 142 is illustrated in the pad 141 in other embodiments, a plurality of separate and distinct holes could be provided in the pad 141, wherein each one of the holes may accommodate a separate second soft tissue cleansing structure 160.

The pad 141 includes an exposed top surface 143. A plurality of projections 144, in the form of nubs, project upward from the top surface 143 of the pad 141. Only a few of the nubs 144 are numerically identified in the figures in order to avoid clutter. As used herein a "nub" is generally meant to include a column-like protrusion (without limitation to the cross-sectional shape of the protrusion) which is upstanding from a base surface. In a general sense, the nub, in the preferred construction, has a height that is greater than the width at the base of the nub (as measured in the longest direction). Nevertheless, nubs could include projections wherein the widths and heights are roughly the same or wherein the heights are somewhat smaller than the base widths. Moreover, in some circumstances (e.g., where the nub tapers to a tip or includes a base portion that narrows to a smaller projection), the base width can be substantially larger than the height.

The nubs 144 are designed to engage the oral soft tissue to significantly reduce a major source of bad breath in people and improve hygiene. The nubs 144 enable removal of microflora and other debris from the tongue and other soft tissue surfaces within the mouth. The tongue, in particular, is prone to develop bacterial coatings that are known to harbor organisms and debris that can contribute to bad breath. This microflora can be found in the recesses between the papillae on most of the tongue's upper surface as well as along other soft tissue surfaces in the mouth. When engaged or otherwise pulled against a tongue surface, for example, the nubs 144 of the first elastomeric tissue cleaner 140 provide for gentle engagement with the soft tissue while reaching downward into the recesses of adjacent papillae of the tongue. The elastomeric construction of the first soft tissue cleaner 140 also enables the top surface 143 of the pad 141 to follow the natural contours of the oral tissue surfaces, such as the tongue, cheeks, lips, and gums of a user. Moreover, the soft nubs 144 are able to flex as needed to traverse and clean the soft tissue surfaces in the mouth along which it is moved.

In the illustrated embodiment, the nubs 144 are preferably conically shaped. As used herein, "conically shaped" or "conical" is meant to include true cones, frusto-conically shaped elements, and other shapes that taper to a narrow end and thereby resemble a cone irrespective of whether they are uniform, continuous in their taper, or have rounded cross-sections. The base portion of each conically shaped nub 144 is larger than the corresponding tip portion.

The pad 141 of the first soft tissue cleaner 140 further comprises a plurality of arcuate ridges 145 formed into the top surface 143. The arcuate ridges 145 are spaced apart from one another in a substantially parallel arrangement along the longitudinal axis A-A of the head. The arcuate ridges 145 extend the entirety of the lateral width of the pad 141, thereby essentially extending form the first lateral edge 126 of the head 120 to the second lateral edge 127 of the head 120. Preferably, the arcuate ridges 145 have a concave side facing the proximal edge 125 of the head 120.

The arcuate ridges 145 are formed by inclined walls 146. The inclined walls 146 preferably extend outward from head 120 in an inclined manner away from the proximal edge 125 of the head 120 and toward the distal end 124 of the head 120. The arcuate ridges 145 are configured to direct fluid in contact with the head 120 toward the lateral edges 126, 127 of the head 120 when the implement 100 is moved across a soft oral tissue. While the structures 145 are described as ridges, they can alternatively be designed and/or considered as arcuate channels. Moreover, while the ridges 145 are illustrated as being arcuate in nature, they take on other shapes and forms, such as linear. In the illustrated embodiment, two of the arcuate ridges 145 are interrupted by the protuberance 180 of the head 120.

The nubs 144 and the ridges 145 collectively form the topography of the first soft tissue cleaner 140. Of course, the topography of the first soft tissue cleaner 140 can take on other forms and structures. It is preferred, however, that the topography of the first soft tissue cleaner 140 be different than the topography of the second and/or third soft tissue cleaners 150, 160.

The exact range of density and/or hardness of the elastomeric material of the first soft tissue cleaner 140 is not limiting of the present invention. In some embodiments, however, the first soft tissue cleaner 140 may be designed to have a different density and/or hardness than the materials of the second and/or third soft tissue cleaners 160, 150.

Furthermore, the resilient material of the first soft tissue cleaner 140 may also be imbued with a sensory material, which can be any suitable biocompatible medication or chemical for oral use. The sensory material is released inside the mouth, lips, or cheeks by way of several methods, including but not limited to abrasion, a temperature change, a change in pH or dissolution. In one embodiment, the sensory material is a sensate that provides a biochemical sensory response to the inside tissue and surfaces of the mouth. Such a sensory response is understood to result from stimulation of the trigeminal nerve of a human. A sensate generally produces a physiological effect without a taste, with such effect usually represented by the terms cooling, tingle, and hot (or heat). Sensates are usually derived from single compounds that are not volatile and that do not have a smell or taste per se. As one example, a chemical known as capsaicin, found naturally in chile peppers, can be used to provide a tingle, a hot or warm massage, or a heating or warm, soothing sensation to a user. Capsaicin is also known to provide pain relief and numbing sensations when topically applied. Some examples of sensates that produce cooling sensations include (–)-menthol and camphor. Most of the polyols, including maltitol syrup, sorbitol, mannitol, erythritol, isomalt and xylitol, also provide a cooling sensation. The coolest of the polyols, erythritol, provides a distinct cooling sensation. Both erythritol and xylitol cool the mouth and fight the sensation of dry mouth commonly associated with prescription drugs and dental hygiene products. Erythritol is a naturally occurring four-carbon structure. Xylitol is a five-carbon sugar found in fruits and vegetables and made in small amounts by the human system as a metabolic intermediate.

In another embodiment, the sensory material is provided as flavoring agent for causing an olfactory sensory response in a human. A flavor agent is commonly understood to include a mixture of compounds that are volatile and produce an aromatic effect and that stimulate the olfactory bulb. Flavors are generally transmitted through the nasal passages, and are often selected and used for their unique association with certain consumer benefits, such as lavender for stress relief or relaxation. Another flavor example is chamomile, which has a strong, aromatic smell and is often used medicinally against sore stomach and as a relaxant to help you fall asleep. Chamomile is also used as a mouthwash against oral mucositis (the swelling, irritation, and ulceration of the mucosal cells that line the digestive tract).

In one embodiment, the first soft tissue cleaner 140 can be imbued with both a sensate component and a flavor component. While the exact sensory material of the elastomeric material of the first soft tissue cleaner 140 is not limiting of the present invention, it is preferred that the first soft tissue cleaner 140 be imbued with a different sensory material than the second and/or third soft tissue cleaners 150, 160.

Referring now to FIGS. 3-6 concurrently, the details of the third soft tissue cleaner 150 will now be discussed. The third soft tissue cleaner 150 is in the form of an elongated strip 151 that is fixed to the peripheral surface 123 of the head 120 of the toothbrush 100. The elongated strip 151 is preferably molded directly to the head 120 but can be molded separately and later fixed to the head 120 if desired. The strip 151 extends about a substantial entirety of the peripheral surface 123 of the head 120. More specifically, the elongate strip 151 extends along the peripheral surface 123 of the head 120 so as to cover the first lateral edge 126, the distal lateral edge 124 and the second distal edge 127 of the head 120.

The elongated strip 151 includes an exposed surface 152. A plurality of channels/grooves 153 are formed into the elongated strip. The grooves 153 are transverse to the axis of the elongated strip 151 and arranged in a spaced-apart manner. Only a few of the grooves 153 are numerically identified in the figures in order to avoid clutter. The grooves 153 form a topography on the surface 152 of the elongated strip of alternating ridges and grooves, which act as massaging microflaps when used.

The third soft tissue cleaner 150 is designed to engage and massage the oral soft tissue to significantly reduce a major source of bad breath in people and improve hygiene (explained in detail above with respect to the first soft tissue cleaner 140). Locating the third soft tissue cleaner 150 on the peripheral surface 123 of the head 120 provides a narrow structure that can be used to reach narrow recesses that the large surface area of the first soft tissue cleaner 140 can not. Moreover, during a normal brushing of teeth, the third soft tissue cleaner 150 will contact the hard to reach crevices between the cheeks and gums.

The grooves 153 (and resulting intermittent ridges) collectively form the topography of the third soft tissue cleaner 150. Of course, the topography of the third soft tissue cleaner 150 can take on other forms and structures. It is preferred, however, that the topography of the third soft tissue cleaner 150 be different than the topography of the first and/or second soft tissue cleaners 140, 160.

The third soft tissue cleaner 150 can be molded to the head 120 (more specifically, the preformed structural body 120A) either in the same shot or separately than the first soft tissue cleaner 140 during an injection molding process.

As is best visible in FIGS. 2 and 6, the first soft tissue cleaner 140 and the third soft tissue cleaner 150 are separated by a wall 170 (comprising sections 170a-e) of the structural body 120A (which is constructed of a hard plastic such as SAN or PP) of the head 120. The wall 170 forms a separation barrier between the first soft tissue cleaner 140 and the third soft tissue cleaner 150. In the illustrated embodiment, the sections 170a-e of the wall 170 are separated by gaps/grooves that are filled with the resilient material of the first and/or third soft tissue cleaner 140, 150. Of course, in other embodiments, the wall 170 may be a continuous structure that completely isolates the first soft tissue cleaner 140 from the third soft tissue cleaner 150.

The exact range of density and/or hardness of the elastomeric material of the third soft tissue cleaner 150 is not limiting of the present invention. The third soft tissue cleaner 150 may be of a different density and/or hardness than the first and/or second soft tissue cleaners 140, 160 in some embodiments. In other embodiments, the third soft tissue cleaner 150 may be of the same density and/or hardness as the first and/or second soft tissue cleaners 140, 160

Furthermore, as discussed above with respect to the first soft tissue cleaner 140, the resilient material of the third soft tissue cleaner 150 may also be imbued with a sensory material. While the exact sensory material of the elastomeric material of the third soft tissue cleaner 150 is not limiting of the present invention, it is preferred that the third soft tissue cleaner 150 be imbued with a different sensory material than the first and/or second soft tissue cleaners 140, 160.

Figure 9:
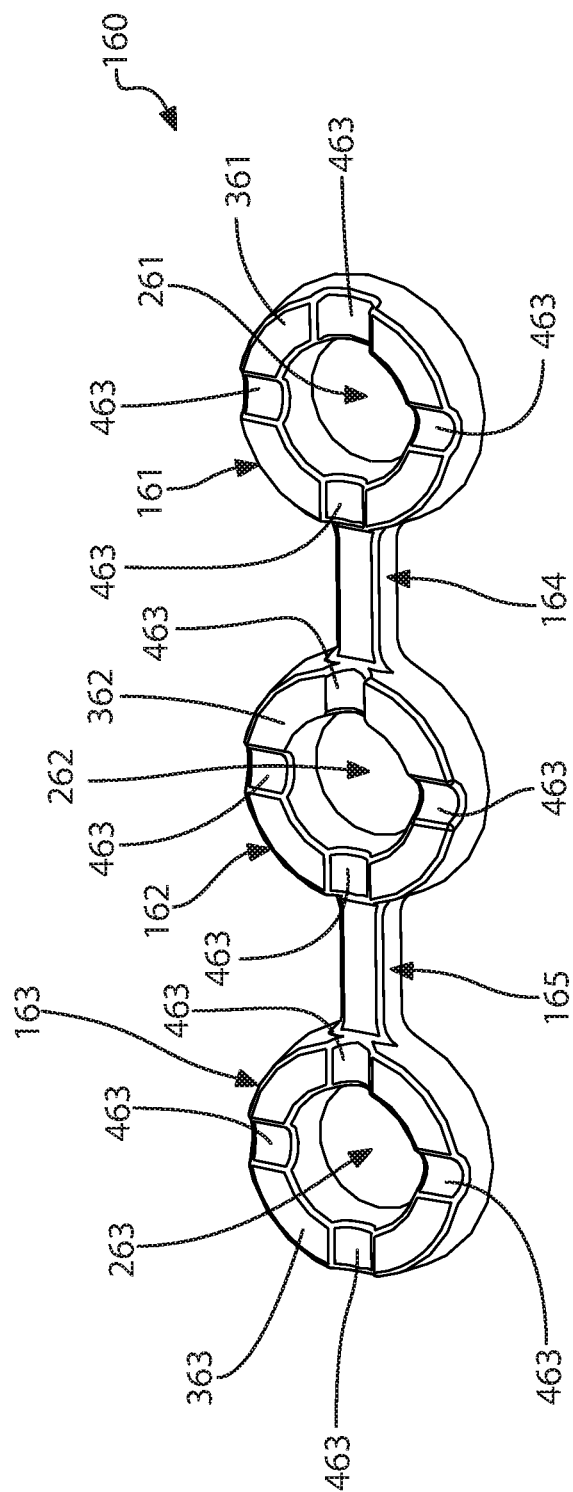
FIG. 9 is a perspective view of a soft tissue cleaner according to an embodiment of the present invention.

Referring now to FIGS. 2, 6 and 9 concurrently, the details of the second soft tissue cleaner 160 and its arrangement on the head 120 will now be discussed. The second soft tissue cleaner 160 is an elastomeric structure comprising three rings 161-163 connected by linear walls 164-165. Of course, more or less rings can be used for the second soft tissue cleaner 160 as desired.

The three rings 161-163 are wall-like structures that form central cavities 261-263 respectively. The three rings 161-163 terminate in top surfaces 361-363 respectively. Each of the rings 361-363 have a plurality of grooves 463 formed into the top surfaces 361-363 in a circumferentially spaced manner.

The second soft tissue cleaner 160 is fixed to the rear surface 122 of the head 120 of the toothbrush 100 so that the rings 161-163 are aligned with the longitudinal axis A-A of the head 120. The second soft tissue cleaner 160 is positioned on that portion of the rear surface 122 of the head 120 that is exposed through the central hole 142 of the first soft tissue cleaner 140. As is best visible in FIGS. 7-8, the second soft tissue cleaner 160 is fixed to a protuberance 180 of the hard plastic (such as SANS or PP) of which the structural body 120A of the head 120 is formed that extends through the central hole 142.

Most preferably, the second soft tissue cleaner 160 is positioned within the central hole 142 (and atop the protuberance 180) so that it is spaced and isolated from the first soft tissue cleaner 140. The second soft tissue cleaner 160 is preferably molded directly to the head 120 but can be molded separately and later fixed to the head 120 if desired. It is also preferred that the second soft tissue cleaner 160 be molded to the head 120 in a second shot separate than the first and third soft tissue cleaners 140, 150.

The second soft tissue cleaner 160 is designed to engage and massage the oral soft tissue to significantly reduce a major source of bad breath in people and improve hygiene (explained in detail above with respect to the first soft tissue cleaner 140). The second soft tissue cleaner 160 is designed and arranged to work in combination with the first soft tissue cleaner 140 during an oral care session to effectively clean a soft tissue surface, especially tongue. More specifically, the second soft tissue cleaner 160 is specifically designed so that the top surfaces 361-363 of the rings 161-163 are at least flush with (and preferably higher) than the tops of the tallest nubs 144 of the first soft tissue cleaner 140. It also preferable that the second soft tissue cleaner 160 be constructed of an elastomeric material that is of a different type than that of the first soft tissue cleaner 140, such as having a different color, flavor, sensate, density and/or hardness. Thus, during movement of the head 120 across the tongue (or other oral surface) the softer first soft tissue cleaner 140 can bend and reach into the recesses between the papillae of the tongue's upper surface and loosen particles while the more rigid second soft tissue cleaner 160 can sweep the particles away and/or finalize the dislodging process.

The rings 161-163 and walls 164-165 collectively form the topography of the second soft tissue cleaner 160. Of course, the topography of the second soft tissue cleaner 160 can take on other forms and structures. It is preferred, however, that the topography of the second soft tissue cleaner 160 be different than the topography of the first and/or third soft tissue cleaners 140, 150. The second soft tissue cleaner 160 protrudes from the top surface of the protuberance 180.

Furthermore, as discussed above with respect to the first soft tissue cleaner 140, the resilient material of the second soft tissue cleaner 160 may also be imbued with a sensory material. While the exact sensory material of the elastomeric material of the third soft tissue cleaner 160 is not limiting of the present invention, the second soft tissue cleaner 160 may be imbued with a different sensory material than the first and/or third soft tissue cleaners 140, 150.

Figure 7:
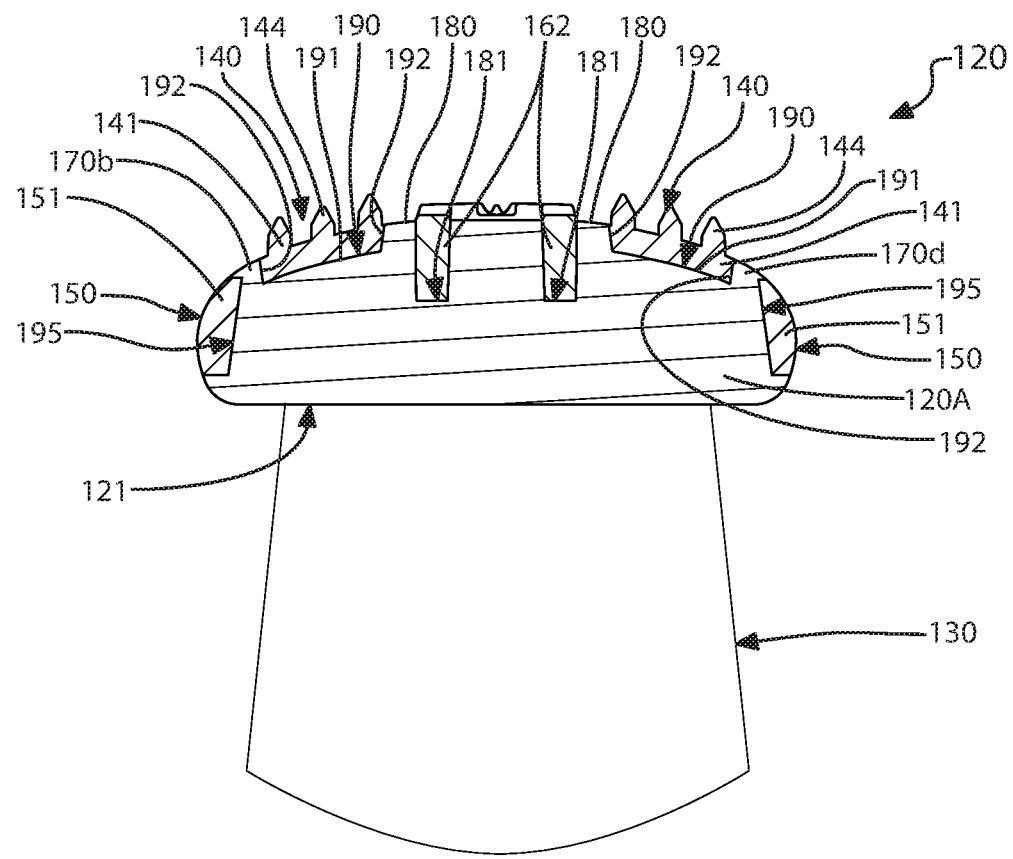
FIG. 7 is a lateral cross-sectional view of the head of the ansate oral care implement of FIG. 1 along view VII-VII of FIG. 6.
Figure 8:
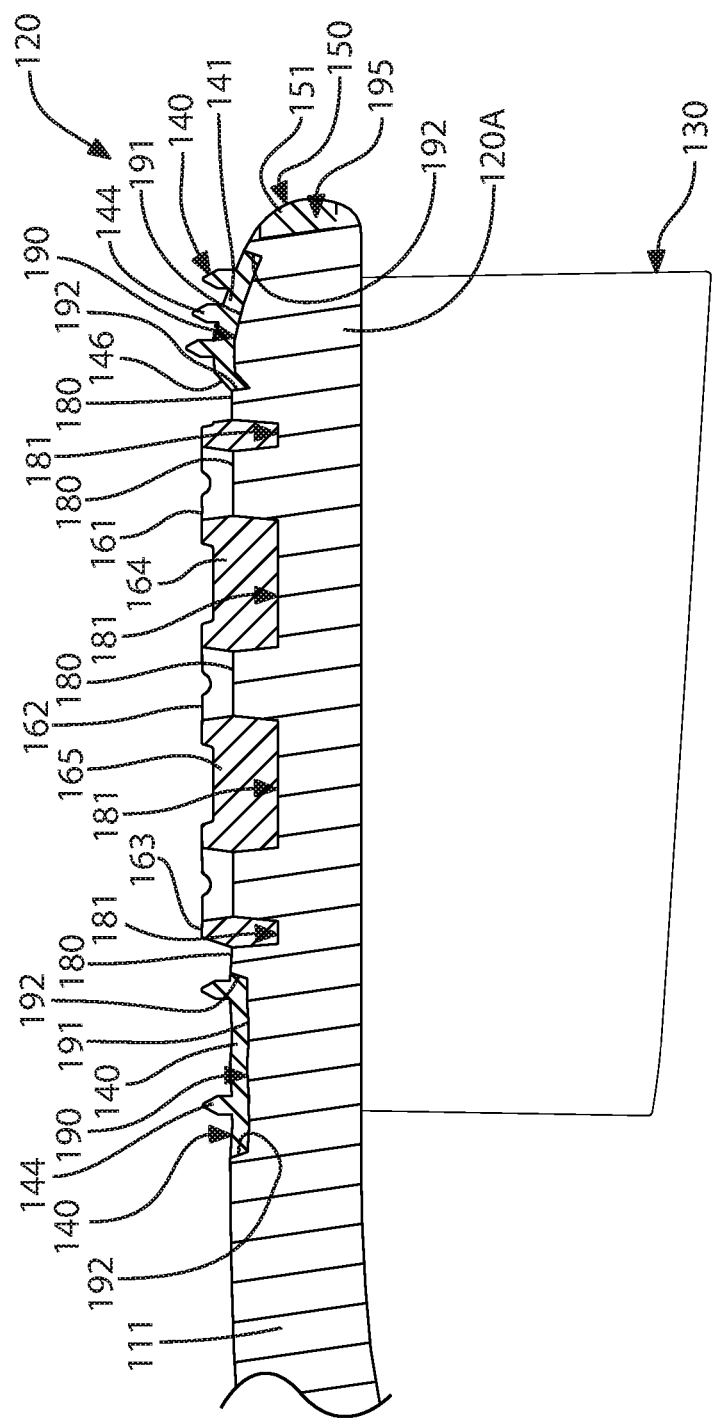
FIG. 8 is a longitudinal cross-sectional view of the head of the ansate oral care implement of FIG. 1 along view VIII-VIII of FIG. 6.

Referring now to FIGS. 7-8 concurrently, the structural details of the connection and arrangement of the cleaners 140, 150, 160 to the structural body 120A of the head 120 will be discussed in greater detail. The rear surface 122 of the structural body 120A of the head 120 comprises a basin 190 formed therein for receiving the first soft tissue cleaner 140. The basin 190 is defined by a recessed floor 191 and upstanding side walls 192. The basin 190 corresponds in size and shape to the first soft tissue cleaner 140 so as to effectuate nesting of the first soft tissue cleaner 140 therein. In the illustrated embodiment, the basin 190 is an annular basin resulting in a protuberance 180 extending centrally upward from a central portion of the floor 191 of the basin 190. As a result, the basin 190 circumferentially surrounds the protuberance 180. The protuberance 180 is an integrally formed extension of the main structural body 120A of the head 120 and corresponds to the size and shape of the central hole 142 of the first soft tissue cleaner 140. The protuberance 180 extends through the central hole 142 of the first soft tissue cleaner 140.

The third soft tissue cleaner 160 is fixed to a top surface of the protuberance 180 and separated from the first soft tissue cleaner 140. In other words, the second soft tissue cleaner 160 is an isolated structure that does not come into contact with the first soft tissue cleaner 140. The second soft tissue cleaner 160 nests within channels 181 formed within the top surface of the protuberance 180. The second soft tissue cleaner 160 is preferably as tall as or extends above the tallest of the nubs 144 of the first soft tissue cleaner 140.

A peripheral channel 195 is also formed into the peripheral surface 123 of the structural body 120A of the head 120. The peripheral channel 195 extends along the lateral surface of the head 120 between the front surface 121 and the rear surface 122. The second soft tissue cleaner 150 nests within the channel 195. A plurality of grooves/gaps are also provided in the rear surface 122 of the structural body 120A that extend between (and connect) the peripheral channel 195 and the basin 190. These grooves (which are in essence gaps between the wall sections 170a-e) make it possible to form the first and third soft tissue cleaners 140, 150 with a single shot of thermoplastic elastomer during the injection molding process.

Referring now to FIGS. 6-8 concurrently, one preferred embodiment of manufacturing the head 120 via an injection molding process will be described. First, the structural head 120A of the head 120 is formed by injecting a liquefied hard plastic, such as PP or SAN, into a mold having the appropriately shaped fill cavity. Once the structural body 120A is sufficiently cooled (the structure of which is described above), an outer mold is placed about the structural body 120A for forming the first and third soft tissue cleaners 140, 150. The first and third soft tissue cleaners 140, 150 are formed by overmolding process which involves injecting a single shot of a first type of liquefied thermoplastic elastomer into the basin 190 at point IP2 via a first port. The first type of liquefied thermoplastic elastomer fills the basin 190 and flows into the peripheral channel 195 (via the gaps/grooves between the wall sections 170a-e), thereby filling the peripheral channel 195. As a result, the first and third soft tissue cleaners 140, 150 are formed as illustrated. Of course, the first and third soft tissue cleaners 140, 150 can be formed with separate shots in other embodiments. The second soft tissue cleaner 160 is formed by injecting a second shot of a second type of liquefied thermoplastic elastomer at point IP1 via a second port. The two ports are both positioned above the head and therefore, the ports are sized so that both can inject separately onto the head. The second port allows the second soft tissue cleaner 160 to be formed on the protuberance 180 in an isolated and spaced manner form the first soft tissue cleaner 140. This allows the first and second soft tissue cleaners 140, 160 to be formed of different types of elastomers. For example, the first and second soft tissue cleaners 140, 160 can have different colors, flavors, sensates or material properties, such as hardness or density.

While a number of embodiments of the current invention have been described and illustrated in detail, various alternatives and modifications will become readily apparent to those skilled in the art without departing from the spirit and scope of the invention. As various changes could be made in the above methods, compositions and structures without departing from the scope of the invention, it is intended that all matter contained in this application, including all mechanisms and/or modes of interaction described above, shall be interpreted as illustrative only and not limiting in any way the scope of the appended claims.

What is claimed is:

1. An oral care implement comprising:
    a handle;
    a head connected to the handle, the head having a first surface, a second surface opposite the first surface, and a peripheral surface extending between the first and second surfaces;
    a soft tissue cleaner comprising:
        a first portion located on the second surface of the head; and
        a second portion located at least partially on the peripheral surface of the head;
    wherein the second portion of the soft tissue cleaner comprises a plurality of grooves that are equidistantly spaced apart from one another and elongated in a direction extending between the first and second surfaces; and
    wherein the first portion of the soft tissue cleaner comprises a plurality of arcuate ridges formed by inclined walls.

2. The oral care implement of claim 1 wherein the first and second portions of the soft tissue cleaner are formed of a resilient material.

3. The oral care implement of claim 1 wherein the first portion of the soft tissue cleaner is a pad having a top surface, and further comprising a plurality of projections extending from the top surface of the pad.

4. The oral care implement of claim 1 wherein the peripheral surface comprises a first lateral edge, a second lateral edge opposite the first lateral edge, and a distal edge, the plurality of grooves being located on the second portion of the soft tissue cleaner along each of the first lateral edge, the second lateral edge, and the distal edge of the peripheral surface.

5. The oral care implement of claim 4 wherein each of the plurality of groves on the first lateral edge is aligned with one of the plurality of grooves on the second lateral edge.

6. The oral care implement of claim 4 wherein the plurality of grooves on the first lateral edge are parallel to one another and the plurality of grooves on the second lateral edge are parallel to one another.

7. The oral care implement of claim 1 wherein the plurality of grooves extend only a portion of the thickness of the second portion of the soft tissue cleaner.

8. The oral care implement of claim 1 wherein each of the plurality of grooves has an arcuate cross-sectional profile.

9. The oral care implement of claim 1 wherein the first and second portions of the soft tissue cleaner are separated by a wall, the wall and the head being an integrally formed monolithic component.

10. The oral care implement of claim 9 wherein the wall is interrupted by a plurality of gaps, the plurality of gaps extending from the first portion of the soft tissue cleaner to the second portion of the soft tissue cleaner, and wherein the plurality of gaps are filled with a resilient material.

11. The oral care implement of claim 1 wherein the inclined walls are symmetric about a longitudinal axis of the head.

12. The oral care implement of claim 1 wherein the inclined walls slope away from the handle with increasing distance from the second surface of the head.

* * * * *